United States Patent [19]

Sartorelli et al.

[11] Patent Number: 4,892,887
[45] Date of Patent: Jan. 9, 1990

[54] N,N'-BIS(SULFONYL)HYDRAZINES HAVING ANTINEOPLASTIC ACTIVITY

[75] Inventors: Alan C. Sartorelli, Woodbridge; Krishnamurthy Shyam, Hamden, both of Conn.

[73] Assignee: Yale University, New Haven, Conn.

[21] Appl. No.: 230,687

[22] Filed: Aug. 9, 1988

Related U.S. Application Data

[60] Continuation of Ser. No. 52,493, May 20, 1987, abandoned, which is a division of Ser. No. 810,644, Dec. 18, 1985, Pat. No. 4,684,747, which is a continuation-in-part of Ser. No. 683,852, Dec. 20, 1984, abandoned.

[51] Int. Cl.⁴ ............................................. A61K 31/18
[52] U.S. Cl. ................................................... 514/601
[58] Field of Search ......................................... 514/601

[56] References Cited

U.S. PATENT DOCUMENTS 3,888,802  6/1975  Hunter ................................. 564/81
4,096,100  6/1978  Hunter et al. ........................ 564/81

Primary Examiner—Anton H. Sutto
Attorney, Agent, or Firm—Ostrolenk, Faber, Gerb & Soffen

[57] ABSTRACT

Compounds of the formula

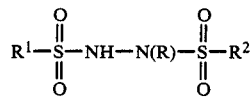

where R is methyl or 2-chloroethyl, and $R^1$ and $R^2$ are each an aromatic hydrocarbon, ring substituted aromatic hydrocarbon moiety, or an alkyl moiety. The compounds have been found to be alkylating agents having antineoplastic activity.

14 Claims, No Drawings

N,N'-BIS(SULFONYL)HYDRAZINES HAVING ANTINEOPLASTIC ACTIVITY

This research was supported in part by a U.S. Public Health Service grant (CA-02817) from the National Cancer Institute.

RELATED APPLICATIONS

This application is a continuation of U.S. Ser. No. 52,493, filed May 20, 1987, now abandoned, which is a division of U.S. Ser. No. 810,644, filed Dec. 18, 1985, now U.S. Ser. No. 4,648,747, which is a c-i-p of U.S. Ser. No. 683,852, filed Dec. 20, 1984, now abandoned.

BACKGROUND OF THE INVENTION

1. Field of the Invention

This invention relates to novel compounds having antineoplastic activity. More specifically, it relates to compounds of the class of N, N'-bis(sulfonyl)hydrazines and their use in inhibiting tumors. These novel compounds constitute a new class of alkylating agents.

2. Prior Art

Alkylating agents capable of methylating biological molecules form a useful group of antineoplastic agents, with procarbazine, streptozotocin and dacarbazine being clinically active agents of this type.

N, N'-bis(sulfonyl)hydrazines are known, although not as having antineoplastic activity. For example, Klös, =Auslegeschrift 1,069,637 discloses N,N'-bis(methylsu]fonyl]hydrazine-($CH_3SO_2NHNHSO_2CH_3$) —and N,N'-bis(n-butylsulfonyl)hydrazine —$C_4H_9SO_2NHNHSO_2C_4H_9$. See also, Munshi et al, Journal of the Indian Chemical Society, Vol. 40, No. 11, 1963, pp. 966–968 and Auslegeschrift 1,023,969 to Müller-Bore (photographic developers). These compounds differ from those claimed herein in that they do not have an alkyl substituent on the hydrazine moiety. This alkyl substituent, as demonstrated herein, is essential for the generation of reactive species necessary for antineoplastic activity.

OBJECTS AND SUMMARY OF THE INVENTION

An object of this invention is to provide a new class of alkylating agents having antineoplastic activity.

A further object is to provide compositions containing such agents in a form suitable for administration to host organisms.

A still further object is to provide a method for preparing the novel alkylating agents.

This invention relates to compounds of the formula:

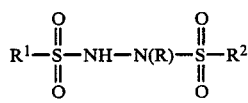

I where R is methyl or 2-chloroethyl and $R^1$ and $R^2$, which may be the same or different, are each an aromatic hydrocarbon moiety or a ring substituted aromatic hydrocarbon moiety, or an alkyl moiety. $R^1$ and/or $R^2$ groups are preferably phenyl, p-tolyl, 2-naphthyl, benzyl, styryl, p-methoxyphenyl, p-chlorophenyl, p-fluorophenyl, p-bromophenyl, p-iodophenyl, p-nitrophenyl, o-nitrophenyl and p-acetylaminophenyl, and alkyl groups of 1–10 carbon atoms such as methyl, ethyl and the like.

The compounds described are useful as alkylating agents having antineoplastic properties and have exhibited pronounced antitumor activity. In addition, they should have low mammalian toxicity. They may suitably be administered to a host organism internally in the form of conventional pharmaceutical preparations, for example in conventional pharmaceutically acceptable enteral or parenteral excipients.

The compounds described, where $R^1$ and $R^2$ are different, and R is methyl, may be prepared by reacting a compound of the formula $R^1SO_2X$, where X is halogen, preferably chlorine, with a compound of the formula $R^2SO_2N(CH_3)NH_2$ in substantially equivalent proportions, where $R^1$ and $R^2$ are as defined above.

Where $R^1$ and $R^2$ are the same, the sulfonyl halide reactant containing that group is used in a ratio of substantially 2:1 with respect to the reactant

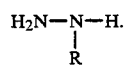

The reaction in each case is carried out in a suitable solvent, e.g. pyridine.

The compound described, where $R^1$ and $R^2$ are the same or different and R is 2-chloroethyl, may be prepared by reacting a compound of the formula $R^2SO_2N(CH_2CH_2OSO_2R^1)NHSO_2R^1$ with lithium chloride in acetone. The former, viz. $R^2SO_2N(CH_2CH_2OSO_2R^1)NHSO_2R^1$, in turn, is prepared by reacting a compound of the formula $R^1SO_2Cl$ with a compound of the formula $R^2SO_2N(CH_2CH_2OH)NH_2$ in a 2:1 molar ratio in a suitable solvent, e.g. pyridine.

DETAILED DESCRIPTION OF THE INVENTION

The compounds described above are a new class of antineoplastic agents. A number of them have been synthesized and tested with demonstrable effectiveness against the L1210 leukemia, P388 leukemia, sarcoma 180 and B16 melanoma transplanted rodent tumors. These compounds possess the capacity to generate an alkylating species under physiological conditions.

From purely chemical considerations, two factors could potentially influence the rate of breakdown of these agents to generate the putative alkylating species (II): (a) the acidity of the hydrazide proton; and (b) the leaving group ability of the sulfinate, $R^2SO_2$- as identified in the following formulas:

$R^1, R^2$=aryl, benzyl, or alkyl group

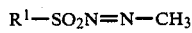

II

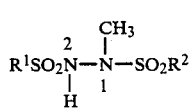

III

In the synthesis and evaluation against the L1210 leukemia of compounds 1–6 and 8 described in Tables I and III, (a) the arenesulfonyl or aralkylsulfonyl group attached to N-2 was varied while keeping the leaving group constant, and (b) the leaving group was changed while keeping the arenesulfonyl moiety attached to N-2 constant. Evidence was found, using a modification of the method of Wheeler and Chumley (J. Med. Chem.

10, 259,1967), incorporated herein by reference, that these compounds decompose in solution to generate species capable of alkylating nucleophiles (see Table II).

Method of Production

Compounds 1-6 (Table I, herein) were prepared by the methodology shown in Scheme A. Compounds 1, 2, 3 and 6 were synthesized by reacting the appropriate arenesulfonyl chloride or aralkylsulfonyl chloride with N-methyl-N-(p-toluenesulfonyl)hydrazide in pyridine. Similarly, the reaction of the appropriate N-methyl-N-arenesulfonylhydrazide with tosyl chloride in pyridine gave compounds 4 and 5. The N-methyl-N-arenesulfonylhydrazides were prepared using a modification of a literature procedure (Friedman et al., Org. Syn., Coll. Vol. 5, 1055, 1973, incorporated herein by reference).

SCHEME A

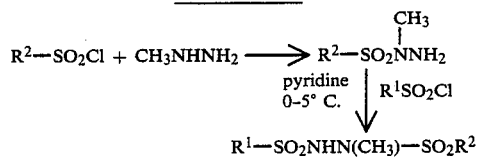

Bis(sulfonyl)hydrazines (compounds 7-11) were prepared by reacting the appropriate sulfonyl chloride with methylhydrazine in about a two to one molar ratio in pyridine. Other solvents may be used, e.g. methylene chloride, chloroform, diethyl ether. The solvent should contain at least two equivalents of base. The reaction is according to Scheme B:

SCHEME B

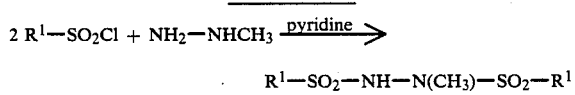

$R^1$—$SO_2$—NH—N($CH_3$)—$SO_2$—$R^1$

The procedure generally followed in the preparation of the N-methyl-N,N'-bis(sulfonyl)-hydrazines of the general structure

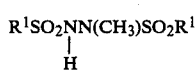

was as follows:
The appropriate sulfonyl chloride (0.02 mol) was added in portions to an ice-cold, stirred solution of methylhydrazine (0.01 mol) in pyridine (4 ml) over a period of 20 minutes. After an additional 30 minutes, the reaction mixture was poured into a mixture of 25 ml of ice and concentrated hydrochloric acid (1:1, v/v). The solid that separated was filtered immediately, washed with cold water and dried. Recrystallization from glacial acetic acid afforded the analytically pure product.

Another procedure followed in preparing the N-methyl-N,N'-bis(sulfonyl)hydrazines was as follows: The appropriate sulfonyl chloride (0.02 mol) was added in portions to an ice-cold stirred solution of methylhydrazine (0.01 mol) in pyridine (4 ml) while maintaining the temperature between 0° and 10° C. After an additional 3 hours, the reaction mixture was poured into a mixture of ice and concentrated hydrochloric acid (1:1 v/v). The solid that separated was filtered immediately, heated with glacial acetic acid (3 ml) at 60° C. and cooled. The precipitate was filtered, washed with cold water and dried. Recrystallization from chloroform-carbon tetrachloride gave the pure compound.

Compounds 12-13 were prepared by reacting the appropriate alkanesulfonyl chloride with N-methyl-N-(p-toluenesulfonyl)hydrazide in a 1:1 molar ratio in pyridine as shown in Scheme C.

SCHEME C

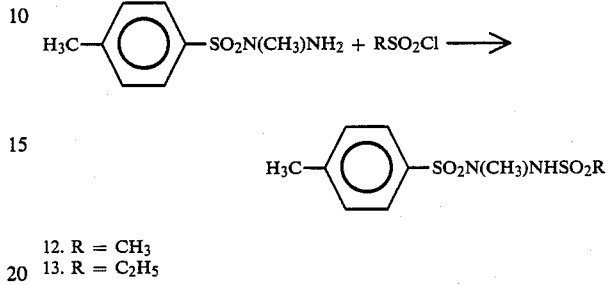

12. R = $CH_3$
13. R = $C_2H_5$

A procedure followed for the preparation of N-2 substituted N-methyl-N-(p-toluenesulfonyl) hydrazides was as follows: The appropriate alkanesulfonyl chloride (0.01 mol) was added in portions to a cold stirred suspension of N-methyl-N-(p-toluene-sulfonyl)hydrazide (0.01 mol) in pyridine (2 ml) while maintaining the temperature between 5° and 15° C. The reaction mixture was allowed to stand in the refrigerator for an additional 24 hours and then was poured into a mixture of ice and concentrated hydrochloric acid (25 ml, 1:1, v/v). The solid that separated was filtered immediately, washed with water, pressed dry and recrystallized from an appropriate solvent.

Physical Properties

Melting points were recorded on a Thomas-Hoover capillary melting point apparatus and are uncorrected. NMR spectra were determined with a Varian T-60A or EM-390 spectrometer with Me$_4$Si as an internal standard. The spectral measurements were as expected; therefore, routine data are not included. Where analyses are indicated by the symbols of elements, the analytical results for those elements were within ± 0.4% of the theoretical values. Pertinent physical data for the compounds synthesized are listed in Table I.

Alkylating Ability

Since compounds 1-13 were conceived as prodrugs of the alkylating species (II), representative compounds of this class, viz. 1-6, 8 and 10 were tested for alkylating ability using a modification of the method of Wheeler and Chumley. This method measured the absorbance at 540 nm of the alkylated product of 4-(4-nitrobenzyl)-pyridine. The data for compounds 1-6, 8 and 10 are listed in Table II.

Tumor-Inhibitory Properties

The tumor-inhibitory properties of compounds 1-12 were determined by measuring their effects on the survival time of mice bearing the L1210 leukemia and in some cases Sarcoma 180, and the P388 leukemia. The results of these tests are summarized in Table III. The ascites cell forms of the L1210 leukemia, Sarcoma 180 and P388 leukemia were propagated in CDF-1 mice. Transplantation was carried out using donor mice bearing 7-day tumor growths; experimental details are described in Agrawal et al., J. Med. Chem., 11, 700, 1968, incorporated herein by reference. Mice were weighed during the course of the experiments, and the percentage change in body weight from the onset to termination of therapy was used as an indication of host toxicity.

The tumor inhibitory properties of compounds 1-13, as shown in Table IV, were also evaluated against the B16 melanoma. This tumor was propagated in C57B1mice. Transplantation was carried out by removing tumors from donor mice bearing 14-day subcutaneous tumor growths. The tissue was fragmented to make a well-dispersed cellular suspension and diluted with Fischer's medium without serum so that one gram of tissue was suspended in 5 ml of solution. A portion (0.2 ml) of the resulting cell suspension was injected intraperitoneally into each recipient animal. All compounds were administered over a wide range of dosage levels by intraperitoneal injection, beginning 24 hours after tumor implantation, once daily for 6 consecutive days. The test compounds were injected as fine suspensions following homogenization in 2 to 3 drops of 20% aqueous Tween 80 and then made up to volume with isotonic saline. All drugs were administered in a volume of 0.5 ml and for any one experiment animals were distributed into groups of five mice of comparable weight and maintained throughout the course of the experiment on Laboratory Chow pellets and water ad libitum. Control tumor bearing animals given injections of comparable volumes of vehicle were included in each experiment. Mice were weighed during the course of the experiments, and the percent change in body weight from onset to termination of therapy was used as an indication of drug toxicity. Determination of the sensitivity of neoplasms to these agents was based on the prolongation of survival time afforded by the drug treatments.

RESULTS
Compounds Tested 1-5, 7-10:

$R^3-\bigcirc-SO_2NHN(CH_3)SO_2-\bigcirc-R^4$

6:

$\bigcirc-CH_2SO_2NHN(CH_3)SO_2-\bigcirc-CH_3$

N—Methyl-N—(p-toluenesulfonyl)-N'—benzylsulfonyl-hydrazine

11:

$\bigcirc\bigcirc-SO_2NHN(CH_3)SO_2-\bigcirc\bigcirc$

N—methyl-N,N'—bis(2-naphthalenesulfonyl)hydrazine 12-13:

$H_3C-\bigcirc-SO_2N(CH_3)NHSO_2R^4$

N'—alkanesulfonyl-N—methyl-N—(p-toluenesulfonyl) hydrazine

The foregoing formulas should be used in conjunction with Table I.

TABLE I

Physical Constants for N—Methyl-N, N'—bis (sulfonyl)-hydrazines

| Compd | $R^3$ | $R^4$ | Yield % | Mp, °C. | Formula |
|---|---|---|---|---|---|
| 1 | H | $CH_3$ | 28 | 171-173 | $C_{14}H_{16}N_2O_4S_2$ |
| 2 | $OCH_3$ | $CH_3$ | 21 | 159-160 | $C_{15}H_{18}N_2O_5S_2$ |
| 3 | Cl | $CH_3$ | 25 | 176-178 | $C_{14}H_{15}ClN_2O_4S_2$ |
| 4 | $CH_3$ | $OCH_3$ | 7 | 192-193 | $C_{15}H_{18}N_2O_5S_2$ |
| 5 | $CH_3$ | Cl | 48 | 174-176 | $C_{14}H_{15}ClN_2O_4S_2$ |
| 6 | — | — | 41 | 185-187 | $C_{15}H_{18}N_2O_4S_2$ |
| 7 | H | H | 36 | 172-173 | $C_{13}H_{14}N_2O_4S_2$ |
| 8 | $CH_3$ | $CH_3$ | 28 | 152-154 | $C_{15}H_{18}N_2O_4S_2$ |
| 9 | $OCH_3$ | $OCH_3$ | 37 | 195-197 | $C_{15}H_{18}N_2O_6S_2$ |
| 10 | Cl | Cl | 13 | 202-204 | $C_{13}H_{12}Cl_2N_2O_4S_2$ |
| 11 | — | — | 37 | 194-195 | $C_{21}H_{18}N_2O_4S_2$ |
| 12 | — | $CH_3$ | 50 | 144-145 | $C_9H_{14}N_2O_4S_2$ |
| 13 | — | $C_2H_5$ | 21 | 135-136 | $C_{10}H_{16}N_2O_4S_2$ |

TABLE II

Degree of Alkylation of 4-(4-Nitrobenzyl) pyridine and Antineoplastic Activity of N,N'—bis (Arenesulfonyl)-or (Aralkylsulfonyl) hydrazines[a]

| Compd | Relative Alkylating Activity[b] | Antineopastic Activity[c] (max. % T/C from Table III) |
|---|---|---|
| 4 | 82 | 113 |
| 8 | 100 | 147 |
| 2 | 95 | 163 |
| 1 | 118 | 163 |
| 26 | 133 | 174 |
| 3 | 135 | 189 |
| 5 | 169 | 141 |
| 10 | 185 | 124 |

[a]A solution of the test sample (12 micromoles) in 1 ml of acetone, 2 ml of distilled water and 1 ml of Tris-HCl buffer (pH 7.4) was incubated with 4-(4-nitrobenzyl) pyridine (148 micromoles in 0.4 ml of acetone) for 1 hr at 37°C. Following additon of 2 ml of acetone and 1.5 ml of 0.25 M NaOH, the material was extracted with 5 ml of ethyl acetate. The absorbance was determined at 540 nm 30 seconds after the addition of the sodium hydroxide solution. The greater the absorbance value, the greater the degree of alkylation
[b]Relative Alkylating activity = (O.D. for test sample/O.D. for compound 8) × 100.
[c]Activity against the L1210 leukemia (see Table III for details).

TABLE III

Effects of N—Methyl-N, N'—bis (sulfonyl) hydrazines on the Survival Time of Mice Bearing the L1210 Leukemia

| Compd | Dose mg/kg[a] | Av. Change wt. % | Average Survival Time of control Animals, days ± CE | Average Survival Time of Treated Animals, days ± SE | % T/C[c] |
|---|---|---|---|---|---|
| 1 | 50 | +2.0 | 9.2 ± 0.2 | 15.0 ± 1.4 | 163 |
|   | 100 | +5.4 |  | 10.6 ± 0.2 | 115 |
|   | 150 | −2.7 |  | 10.8 ± 0.5 | 117 |
| 2 | 50 | +7.7 | 9.2 ± 0.2 | 10.8 ± 0.6 | 117 |
|   | 100 | +7.8 |  | 15.0 ± 2.3 | 163 |
|   | 150 | +2.9 |  | 13.2 ± 2.2 | 143 |
| 3 | 50 | +3.7 | 9.2 ± 0.2 | 17.4 ± 1.4 | 189 |
|   | 100 | +10.0 |  | 10.8 ± 0.6 | 117 |
|   | 150 | +6.0 |  | 11.2 ± 1.3 | 122 |
| 4 | 50 | +12.6 | 9.2 ± 0.2 | 10.2 ± 0.5 | 111 |
|   | 100 | +14.8 |  | 10.2 ± 0.2 | 111 |
|   | 150 | +9.8 |  | 10.4 ± 0.2 | 113 |
| 5 | 50 | +5.1 | 9.2 ± 0.2 | 10.4 ± 0.4 | 113 |
|   | 100 | +5.5 |  | 13.0 ± 2.2 | 141 |
|   | 150 | −4.6 |  | 10.0 ± 0.3 | 109 |
| 6 | 50 | +10.8 | 9.2 ± 0.2 | 16.0 ± 3.4 | 174 |
|   | 100 | +2.4 |  | 12.6 ± 0.8 | 137 |
|   | 150 | −4.3 |  | 14.6 ± 1.9 | 159 |
| 7[d] | 50 | −4.8 | 9.0 ± 0.0 | 13.2 ± 0.7 | 147 |
|   | 100 | −5.2 |  | 11.6 ± 0.2 | 129 |
|   | 150 | −13.5 |  | 9.4 ± 0.4 | 104 |
| 8[e] | 50 | +3.7 | 9.5 ± 0.3 | 14.0 ± 1.3 | 147 |
|   | 100 | +0.8 |  | 13.6 ± 2.4 | 143 |
| 9[f] | 50 | +10.9 | 9.0 ± 0.0 | 13.4 ± 1.0 | 149 |

TABLE III-continued

Effects of N—Methyl-N, N'—bis (sulfonyl) hydrazines on the Survival Time of Mice Bearing the L1210 Leukemia

| Compd | Dose mg/kg[a] | Av. Change wt. % | Average Survival Time of control Animals, days ± CE | Average Survival Time of Treated Animals, days ± SE | % T/C[c] |
|---|---|---|---|---|---|
|  | 100 | +1.9 |  | 13.2 ± 1.1 | 147 |
|  | 150 | −1.6 |  | 12.2 ± 1.2 | 136 |
| 10 | 50 | +4.1 | 9.5 ± 0.3 | 9.2 ± 0.2 | 97 |
|  | 100 | +4.0 |  | 11.4 ± 0.8 | 120 |
|  | 150 | +1.3 |  | 11.8 ± 1.1 | 124 |
| 11 | 50 | +6.9 | 9.0 ± 0.9 | 11.4 ± 1.1 | 127 |
|  | 100 | +3.0 |  | 10.2 ± 0.4 | 113 |
|  | 150 | −3.3 |  | 14.0 ± 2.3 | 156 |
| 12 | 10 | +9.1 | 9.2 ± 0.2 | 14.8 ± 0.4 | 161 |
|  | 20 | −2.0 |  | 15.0 ± 0.7 | 163 |
|  | 30 | −7.9 |  | 19.2 ± 2.0 | 209 |

[a]Administered once daily for six consecutive days, beginnning 24 hrs. after tumor transplantation, with 5 animals being used per group.
[b]Average change in body weight from onset to termination of therapy.
[c]% T/C = average survival time of treated/control animals × 100. Each value represents the average of 5 animals per group.
[d]Max. % T/C vs. Sarcoma 180 = 203 at 100 mg/kg.
[e]Max. % T/C vs. Sarcoma 180 = 197 at 50 mg/kg.
[f]Max. % T/C vs. P388 leukemia = 136 at 150 mg/kg.

TABLE IV

Effects of N—Methyl-N, N'—bis (sulfonyl) hydrazines on the Survival Time of Mice Bearing the B16 Melanoma.

| Compd | Optimum Effective Daily Dose, mg/kg[a] | Av. Change in wt., %[b] | Max. % T/C[c] |
|---|---|---|---|
| 1 | 150 | +8.5 | 168 |
| 2 | 100 | +9.1 | 200 |
| 3 | 50 | +2.9 | 171 |
| 4 | 100 | −14.0 | 151 |
| 5 | 50 | −0.4 | 162 |
| 6 | 50 | −2.4 | 172 |
| 7 | 100 | −2.3 | 175 |
| 8 | 150 | −2.7 | 165 |
| 9 | 100 | +2.4 | 191 |
| 10 | 50 | +4.8 | 163 |
| 11 | 100 | +4.6 | 164 |
| 12[d] | 10 | −1.9 | 207 |
| 13 | 50 | −1.1 | 174 |

[a]Administered once daily for six consecutive days, beginnign 24 hours after tumor transplanation, with 5 animals being used per group.
[b]Average change in body weight from onset to termination of therapy.
[c]% T/C = average survival time of treated/control animals × 100. Each value represents the average of 5 animals per group.
[d]% T/C values at daily dosages of 10 and 20 mg/kg were both 206.

Additional compounds were synthesized and their antineoplastic activities determined pursuant to the procedures previously described. The results are shown in Table V. Of the compounds tested, Compounds No. 29 and 64 gave the highest increases in survival time against the L1210 leukemia and the B16 melanoma, respectively.

TABLE V

In vivo effects and melting points (uncorrected) of N—methyl-N,N'—bis(sulfonyl)hydrazines $R^1SO_2NHN(CH_3)SO_2R^2$

| No | $R^1$ | $R^2$ | Max. % T/C L1210 Leukemia | Max. % T/C B16 Melanoma | MP °C. |
|---|---|---|---|---|---|
| 4 | p-Tolyl | Phenyl | 153 | 178 | 153–155 |
| 15 | p-Methoxyphenyl | Phenyl | 136 | 191 | 141–142 |
| 16 | p-Chlorophenyl | Phenyl | 122 | 148 | 144–145 |
| 17 | Benzyl | Phenyl |  |  | 133–135 |
| 18 | 2-Naphthyl | Phenyl |  | 181 | 175–177 |
| 19 | p-Bromophenyl | Phenyl |  | 187 | 145–147 |
| 20 | p-Bromophenyl | p-Tolyl | 169 | 161 | 182–184 |
| 21 | 2-Naphthyl | p-Tolyl | 134 |  | 192–194 |
| 22 | p-Nitrophenyl | p-Tolyl |  | 192 | 209–211 |
| 23 | Phenyl | p-Methoxyphenyl | 178 | 151 | 143–144 |
| 24 | p-Chlorophenyl | p-Methoxyphenyl |  | 170 | 144–145 |
| 25 | p-Bromophenyl | p-Methoxyphenyl | 134 | 205 | 149–152 |
| 26 | o-Nitrophenyl | p-Methoxyphenyl |  | 158 | 164–166 |
| 27 | 2-Naphthyl | p-Methoxyphenyl |  | 163 | 187–189 |
| 28 | Benzyl | p-Methoxyphenyl | 152 | 160 | 166–167 |
| 29 | Methyl | p-Methoxyphenyl | 274 | 204 | 126–128 |
| 30 | Ethyl | p-Methoxyphenyl | 149 |  | 110–112 |
| 31 | Phenyl | p-Chlorophenyl | 111 | 146 | 192–194 |
| 32 | p-Methoxyphenyl | p-Chlorophenyl | 130 | 153 | 193–195 |
| 33 | 2-Naphthyl | p-Chlorophenyl | 109 | 153 | 205–207 |
| 34 | 2-Styryl | p-Chlorophenyl |  | 143 | 171–172 |
| 35 | Methyl | p-Chlorophenyl | 167 | 194 | 176–178 |
| 36 | Ethyl | p-Chlorophenyl |  | 164 | 144–146 |
| 37 | Phenyl | p-Bromophenyl |  | 160 | 200–202 |
| 38 | p-Tolyl | p-Bromophenyl | 127 |  | 185–187 |
| 39 | p-Methoxyphenyl | p-Bromophenyl | 165 | 167 | 203–205 |
| 40 | p-Chlorophenyl | p-Bromophenyl |  | 145 | 209–210 |
| 41 | p-Bromophenyl | p-Bromophenyl | 183 | 161 | 215–216 |
| 42 | 2-Naphthyl | p-Bromophenyl |  | 146 | 205–209 |
| 43 | 2-Styryl | p-Bromophenyl |  | 178 | 163–164 |
| 44 | Methyl | p-Bromophenyl |  | 221 | 179–181 |
| 45 | Phenyl | 2-Naphthyl | 106 | 163 | 187–188 |
| 46 | p-Tolyl | 2-Naphthyl | 120 |  | 179–180 |
| 47 | p-Methoxyphenyl | 2-Naphthyl |  |  | 183–185 |
| 48 | p-Chlorophenyl | 2-Naphthyl |  |  | 190–193 |
| 49 | Phenyl | Benzyl | 185 | 208 | 185–187 |

TABLE V-continued

In vivo effects and melting points (uncorrected) of N—methyl-N,N'—bis(sulfonyl)hydrazines
R¹SO₂NHN(CH₃)SO₂R²

| No | R¹ | R² | Max. % T/C L1210 Leukemia | Max. % T/C B16 Melanoma | MP °C. |
|---|---|---|---|---|---|
| 50 | p-Tolyl | Benzyl | 144 | 206 | 179–181 |
| 51 | p-Methoxyphenyl | Benzyl | | 182 | 165–166 |
| 52 | p-Chlorophenyl | Benzyl | 128 | 184 | 195–196 |
| 53 | p-Bromophenyl | Benzyl | | 163 | 201–203 |
| 54 | 2-Naphthyl | Benzyl | 115 | | 174–177 |
| 55 | Benzyl | Benzyl | | 152 | 208–210 |
| 56 | Methyl | Benzyl | | 203 | 166–168 |
| 57 | 2-Styryl | 2-Styryl | | 171 | 181–182 |
| 58 | P-Bromophenyl | p-Acetylaminophenyl | | 164 | 134–136 |
| 59 | p-Tolyl | p-Iodophenyl | 123 | 176 | 196–197 |
| 60 | p-Methoxyphenyl | p-Iodophenyl | | | 191–193 |
| 61 | p-Chlorophenyl | p-Iodophenyl | | | 217–219 |
| 62 | Methyl | p-Iodophenyl | | 195 | 180–182 |
| 63 | Ethyl | p-Iodophenyl | | | 166–167 |
| 64 | p-Tolyl | p-Methyl | | 246 | 131–133 |

Discussion of Results

Determination of the sensitivity of ascitic neoplasms to these agents was based upon the prolongation of survival time afforded by the drug treatments. The compounds that gave the highest and lowest absorbance values in the alkylating activity assay, compounds 10 and 4, were virtually inactive against the L1210 leukemia. It is theorized that compound 10 is inactivated prior to reaching an intracellular site of action, due to its rapid decomposition to a reactive species. Compounds 3 and 5, two other chloro-containing compounds, decomposed less rapidly than compound 10 and were active against the L1210 leukemia. The reason for the relative inactivity of compound 4 is not easy to explain, especially in view of the fact that compound 2, which does not give an appreciably different degree of alkylation with the trapping agent, 4-(4-nitrobenzyl)pyridine, is an active anticancer agent (% T/C=163 at 100 mg/kg). In general, however, there appears to be a correspondence between the capacity to generate a reactive intermediate and activity against the L1210 leukemia. The lack of an absolute correlation, however, implies that an optimal rate of breakdown to an alkylating species is not the only necessary condition for antineoplastic activity against the L1210 leukemia.

Most of the compounds tested displayed at least some activity against the L1210 leukemia; the most active agents increased the survival time of tumor-bearing animals between 41% and 89%. The antineoplastic activity of compounds 1–6 and 8 against the L1210 leukemia was evaluated mainly with a view to studying the effect of varying the acidity of the hydrazide proton on antineoplastic activity. No clear-cut correlation between the acidity of the hydrazide proton and antineoplastic activity could be discerned in this system. Thus, the level of activity displayed by compound 6, in which an aralkyl group is attached to —NH, is comparable to that of compounds 1–3 and 5. There was also no discernible correlation between the leaving group ability of the arenesulfonyl substitution and activity against the L1210 leukemia. Thus, it is likely that the alkylation mechanisms in the proposed involves complex kinetics, since the two arenesulfonyl substituents function as leaving groups in two different reactions (i.e., an elimination reaction whereby the putative alkylating species is generated, and a substitution reaction whereby the nucleophile is alkylated). Furthermore, one cannot rule out the importance of pharmacodynamic mechanisms in the antitumor measurements.

It has been found that replacement of the arylsulfonyl group attached to N-2 by benzenesulfonyl resulted in retention of activity against the L1210 leukemia in mice. Thus, compound 6 (Table III) increased the survival time of mice bearing the L1210 leukemia by 74% at its optimal daily dosage level. Since the interposition of a methylene group between the sulfonyl and aryl moieties would be expected to lower the acidity of the hydrazide proton compared to compounds of structure IV.

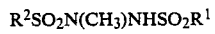

$R_1$ and $R_2$ are aryl

The relatively high level of activity displayed by compound 6 was considered worthy of further investigation. Such a modification would also be expected to influence the alkylating ability of the putative intermediate V generated by the base-catalyzed elimination of the parent molecule:

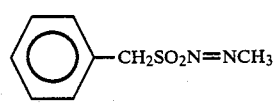

To further understand the structural features that are essential for the antineoplastic activity of this class of agents, compounds 12 and 13 were synthesized and evaluated for antitumor activity against both the L1210 leukemia and the B16 melanoma The antineoplastic properties of compound 12 were determined by measuring its effects on the survival time of mice bearing the L1210 leukemia and the B16 melanoma. Compound 13 was tested against the B16 melanoma only. The results of these tests are shown in Tables III and IV. Both the N-alkanesulfonyl-N'-arenesulfonyl-N'-methylhydrazines examined displayed appreciable levels of activity against the B16 melanoma Compound 12 also displayed a high level of activity against the L1210 leukemia. Replacement of the p-toluenesulfonyl moiety attached to N-2 in compound 8 by methanesulfonyl to give compound 12 not only increased the survival time of tumor-bearing mice significantly, but also produced an increase in potency. Thus, while compound 8 was found to be active against the B16 melanoma in the 50–150 mg/kg dosage range, compound 12 displayed its effectiveness in the 10–30 mg/kg range and was toxic at higher dosage levels. Furthermore, the methanesulfonyl analogue was approximately four-times more toxic to the B16 melanoma cells in culture than compound 8. Since methanesulfinate would be expected to be a poorer leaving group than p-toluenesulfinate, the lower reactivity and hence, greater selectivity of the alkylating species (VI) generated from compound 12 compared to that generated from compound 8 could be a possible reason for the enhanced potency of compound 12.

$$CH_3N=NSO_2CH_3 \qquad VI$$

Cytotoxicity

The cytotoxicity of compounds 8 and 12 was determined by measuring their effects on the colony-forming ability of B16 melanoma cells. The cells were maintained in Eagle's minimum essential medium supplemented with 10% fetal bovine serum. To obtain exponentially growing B16 melanoma cells, a 25 cm² flask was inoculated with 10⁵ cells for two days before addition of drug. The cell monolayer was exposed to various concentrations of compound for 1 hour. After exposure, the layer was washed twice with PBS to remove the compound. The cells were harvested with 2 mM EDTA in PBS, and 200 cells were plated on a 60 mm dish with 5 mL of medium. After incubation for 12 days, the colonies were stained with crystal violet and counted. The surviving fraction of drugtreated cells was calculated by normalizing the results to those of vehicle treated cells that had a cloning efficiency of 48 to 76 percent. The LD50 was determined from the individual dose-response curves. The LD50 for compound 12 was $6.2 \times 10^{-4}$ mM (average of two determinations), and the LD50 for compound 13 was $1.6 \times 10^{-4}$ mM (average of two determinations).

In addition to the compounds listed above, this invention also extends to the following compounds:

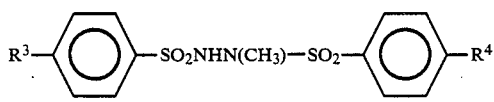

65. $R^3 = F$; $R^4 = CH_3$
66. $R^3 = CH_3$; $R^4 = F$

The invention also extends to the chloroethyl analogues of the compounds disclosed herein. These analogues have the general formula:

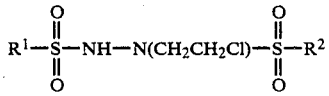

Where $R^1$ and $R^2$ are as defined above. These compounds can be prepared by the methodology shown in Scheme D.

SCHEME D

-continued
SCHEME D

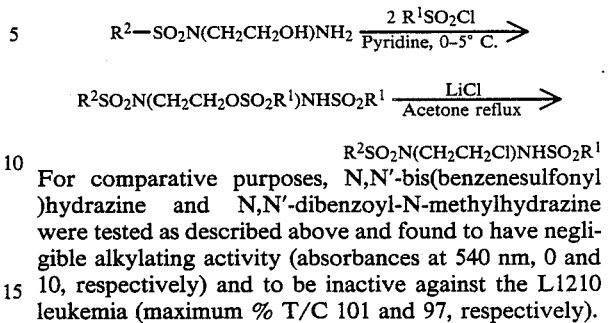

For comparative purposes, N,N'-bis(benzenesulfonyl)hydrazine and N,N'-dibenzoyl-N-methylhydrazine were tested as described above and found to have negligible alkylating activity (absorbances at 540 nm, 0 and 10, respectively) and to be inactive against the L1210 leukemia (maximum % T/C 101 and 97, respectively).

It is theorized that the mechanism for achieving activity in the claimed compounds is as follows:

SCHEME E

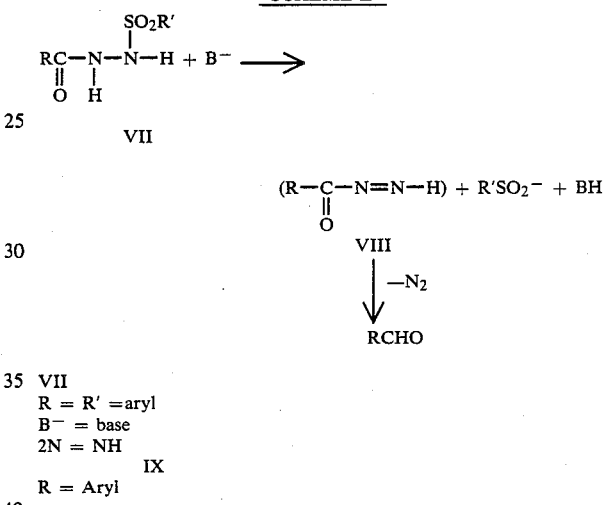

VII
R = R' = aryl
B⁻ = base
2N = NH
IX
R = Aryl

SCHEME F

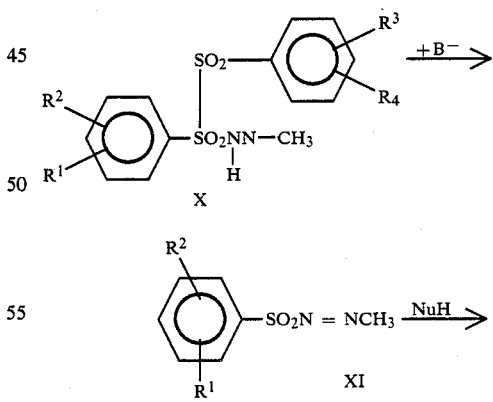

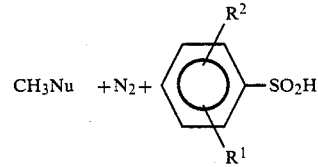

Nu = nucleophile

N-Acyl-N'-(arenesulfonyl)hydrazines (VII in Scheme E) are decomposed by bases to form aldehydes in moderate yields (McFadven et. al., J Chem. Soc., 584, 1936); this reaction often proceeds at high temperatures (Mosettig, Org. React. 8, 234, 1954). Replacement of the acyl group in compound VII by an arenesulfonyl moiety, to form an N,N,'-bis(arenesulfonyl)hydrazine, enhances the acidity of the proton beta to the leaving group and a reaction analogous to the one depicted in Schemes E and F can occur with greater facility. The reaction intermediate in this case is IX, and the product an arenesulfinic acid. Referring to Scheme E, while the compound IX would be expected to lose a molecule of nitrogen readily to give the corresponding arenesulfinic acid, a compound or intermediate such as XI in Scheme F, generated from the precursor molecule X in Scheme F would be less prone to such decomposition. Furthermore, since arenesulfinate is a good leaving group, compound X may function as an alkylating agent in a manner analogous to the N-alkyl-N-nitrosoureas, which generate as biological alkylating agents, alkanediazohydroxides.

The inactivity of N,N'-bis(benzenesulfonyl)hydrazine emphasizes the importance of the methyl group on the hydrazide nitrogen and is consistent with the mechanism of activation proposed in Scheme F. N,N'-dibenzoyl-N-methylhydrazine, which also was inactive against the L1210 leukemia, should not be an effective generator of an alkylating species, since the hydrazide proton is not sufficiently acidic to be abstracted at physiological temperature and pH and, in addition, the benzoyl anion is a relatively poor leaving group.

The compounds of this invention are especially useful in tumor chemotherapy, having been found active against sarcoma 180, leukemia L1210, leukemia P388 and B16 melanoma in mice.

The compounds of this invention are preferably administered internally, e.g., intravenously, in the form of conventional pharmaceutical preparations, for example in conventional enteral or parenteral pharmaceutically acceptable excipients containing organic and/or inorganic inert carriers, such as water, gelatin, lactose, starch, magnesium stearate, talc, plant oils, gums, alchol, Vaseline, or the like. The pharmaceutical preparations can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for tne adjustment of osmotic pressure. The pharmaceutical preparations may also contain other therapeutically active materials.

The pharmaceutical preparation should include an amount of a compound of this invention effective for antineoplastic activity. The effective dosage will depend on the antineoplastic activity and toxicity of the particular compound employed and is thus within the ordinary skill of the art to determine for any particular host mammal or other host organism. Suitable dosages may be, for example, in the range of about 2–15 mg per kg for man.

Typical compounds of the present invention include:
N-(p-chlorobenzenesulfonyl)-N'-methanesulfonyl-N-methylhydrazine;
N'-(p-chlorobenzenesulfonyl)-N-(p-methoxybenzenesulfonyl)-N-methylhydrazine;
N'-(p-chlorobenzenesulfonyl)-N-methyl-N-(2-naphthalenesulfonyl)hydrazine;
N'-benzenesulfonyl-N-benzylsulfonyl-N-methylhydrazine;
N'-benzenesulfonyl-N-(p-bromobenzenesulfonyl)-N-methylhydrazine;
N,N'-bis(p-bromobenzenesulfonyl)-N-methylhydrazine;
N-(p-bromobenzenesulfonyl)-N'-(p-methoxybenzenesulfonyl)-N-methylhydrazine;
N-(p-bromobenzenesulfonyl)-N-methyl-N-(2-naphthalenesulfonyl)hydrazine;
N-(p-bromobenzenesulfonyl)-N'-(p-chlorobenzenesulfonyl)-N-methylhydrazine;
N-(p-bromobenzenesulfonyl)-N-methyl-N'-(2-styrenesulfonyl)hydrazine;
N-(p-acetylaminobenzenesulfonyl)-N'p-bromobenzenesulfonyl)-N-methylhydrazine;
N,N'-bis(benzenesulfonyl)-N-methylhydrazine;
N,N'-bis (4-toluenesulfonyl)-N-methylhydrazine;
N,N'-bis (p-methoxybenzenesulfonyl)-N-methylhydrazine;
N,N'-bis (p-chlorobenzenesulfonyl)-N-methylhydrazine;
N,N'-bis (2-naphthalenesulfonyl)-N-methylhydrazine;
N'-benzenesulfonyl-N-methyl-N-(p-toluenesulfonyl)hydrazine;
N'-(p-methoxybenzenesulfonyl)-N-methyl-N-(p-toluenesulfonyl)hydrazine;
N'-(p-chlorobenzenesulfonyl)-N-methyl-N-(p-toluenesulfonyl)hydrazine;
N'-benzylsulfonyl-N-methyl-N-(p-toluenesulfonyl)hydrazine;
N'-benzenesulfonyl-N-methyl-N-(2naphthalenesulfonyl)hydrazine;
N,N'-bis(benzylsulfonyl)-N-methylhydrazine;
N'-benzenesulfonyl-N-(p-chlorobenzenesulfonyl)-N-methylhydrazine;
N-(p-chlorobenzenesulfonyl)-N'-(p-methoxybenzenesulfonyl)-N-methylhydrazine;
N-(p-chlorobenzenesulfonyl)-N-methyl-N'-(2-naphthalenesulfonyl)hydrazine;
N-(p-chlorobenzenesulfonyl)-N-methyl-N'-(p-toluenesulfonyl)hydrazine;
N-(p-bromobenzenesulfonyl)-N-methyl-N'-(p-toluenesulfonyl)hydrazine;
N'-(p-bromobenzenesulfonyl)-N-methyl-N-(p-toluenesulfonyl)hydrazine;
N-(N'-naphthalenesulfonyl)-N-methyl-N'-(p-toluenesulronyl)hydrazine;
N'-(2-naphthalenesulfonyl)-N-methyl-N-(p-toluenesulfonyl)hydrazine; and the corresponding 1-(2-chloroethyl) analogues.

Although the invention has been specifically described with reference to particular embodiments, it is to be understood that the invention is not limited to the particulars disclosed and extends to all equivalents within the scope of the claims.

What is claimed is:

1. A method of inhibiting tumors in host organisms which comprises administering to a said host organism an antineoplastically effective amount of the compound of the formula

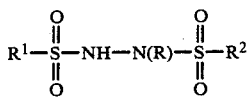

where R is selected from the group consisting of methyl and 2-chloroethyl, and $R^1$ and $R^2$, which may be the same or different, are each a $C_{1-10}$ alkyl, phenyl naphthyl moiety, or a ring substituted, phenyl or naphthyl in which the substituent is methyl, ethenyl, methoxy, halo, nitro, or acetylamino.

2. A method of treating tumors in host organisms according to claim 1 which comprises administering to said host organism an antineoplastically effective amount of the compound where R is methyl.

3. A method of treating tumors in host organisms according to claim 2 which comprises administering to said host organism an antineoplastically effective amount of the compound where $R^1$ and $R^2$ are each selected from the group consisting of phenyl, p-tolyl, 2-naphthyl, benzyl, 2-styryl, p-methoxyphenyl, p-chlorophenyl, p-fluorophenyl, p-acetylaminophenyl, p-iodophenyl, p-nitrophenyl and methyl.

4. The method of claim 3 where $R^1$ and $R^2$ are both phenyl.

5. The method of claim 3 where $R^1$ and $R^2$ are both p-tolyl.

6. The method of claim 3 where $R^1$ and $R^2$ are both p-methoxyphenyl.

7. The method of claim 3 where $R^1$ and $R^2$ are both p-chlorophenyl.

8. The method of claim 3 where $R^1$ and $R^2$ are both 2-naphthyl.

9. The method of claim 3 where $R^1$ is phenyl and $R^2$ is p-tolyl.

10. The method of claim 3 where $R^1$ is p-methoxyphenyl and $R^2$ is p-tolyl.

11. The method of claim 3 where $R^1$ is p-chlorophenyl and $R^2$ is p-tolyl.

12. The method of claim 3 where $R^1$ is p-tolyl and $R^2$ is p-methoxyphenyl.

13. The method of claim 3 where $R^1$ is p-tolyl and $R^2$ is p-chlorophenyl.

14. The method of claim 3 where $R^1$ is benzyl and $R^2$ is p-tolyl.

* * * * *